United States Patent
Elsberry

(10) Patent No.: US 7,069,634 B1
(45) Date of Patent: Jul. 4, 2006

(54) METHOD FOR MANUFACTURING A CATHETER

(75) Inventor: Dennis D. Elsberry, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/512,777

(22) Filed: Feb. 24, 2000

Related U.S. Application Data

(62) Division of application No. 08/912,379, filed on Aug. 18, 1997, now Pat. No. 6,093,180, which is a division of application No. 08/782,551, filed on Jan. 10, 1997, now abandoned, which is a division of application No. 08/430,960, filed on Apr. 28, 1995, now abandoned.

(51) Int. Cl.
B23P 11/02 (2006.01)

(52) U.S. Cl. .................. 29/447; 604/506; 604/151; 604/264; 604/523; 128/898; 128/DIG. 12

(58) Field of Classification Search ............ 29/447, 29/450; 604/8, 9, 19, 20, 48, 508, 510, 514, 604/515, 516, 517, 73, 93, 117, 123, 131, 604/264–266, 275, 523, 892.1, 506, 528, 604/530, 531, 533, 534–536; 128/DIG. 12, 128/898
See application file for complete search history.

(56) References Cited

U.S. PATENT DOCUMENTS

| 1,852,351 A | | 4/1932 | Lewis | |
|---|---|---|---|---|
| 3,123,072 A | * | 3/1964 | Bellamy, Jr. | 29/447 |
| 3,470,604 A | * | 10/1969 | Zenick | 29/447 |

(Continued)

FOREIGN PATENT DOCUMENTS

| WO | WO 94/15663 | 7/1994 |
|---|---|---|
| WO | WO 94/26341 | 11/1994 |

OTHER PUBLICATIONS

"Stereotactic Neurosurgery", Critical Reviews in Biomedical Engineering, by Robert L. Galloway and Robert J. Maciunas, 1990, vol. 18, Issue 3, pp. 181–205.

"Intraputaminal Infusion of Nerve Growth Factor to Support Adenal Medullary Autografts in Parkinson's Disease", Arch Neurol, by Olson et al., Apr. 1991, vol. 48, pp. 373–381.

"Intraspinal Drug Delivery" Surgical Technique Notebook, Synchromed® Infusion System Medtronic Product Manual, UC 9100612bEN NP–1330b, Medtronic, Inc. 1992.

"New Alzheimer's Therapy Suggested" Science, vol. 260, Jun. 18, 1993, pp. 1719–1720.

*Primary Examiner*—S. Thomas Hughes
*Assistant Examiner*—Jermie E. Cozart
(74) *Attorney, Agent, or Firm*—Curtis D. Kinghorn; Hal R. Patton; Tom G. Berry

(57) ABSTRACT

An intraparenchymal infusion catheter system for delivering drugs or other agents to selected sites in an organism, such as a human, includes a pump that may be implanted or disposed outside the organism. A catheter is coupled to the pump. The catheter comprises a flexible biocompatible tubular portion terminating in a free distal end. The distal end of the catheter bears a rounded tip, a portion of which is slidably disposed within the lumen of the tubular portion. The tip is porous for discharging an agent or drug to a selected site. The tip has a microporosity of less than or equal to 0.22 microns. The tubular portion is composed from a material that will expand from its nominal size when exposed to a stimulus such as heat or a solvent and return to its nominal size when the stimulus is withdrawn. By expanding the tubular portion, a physician can select the amount of the tip that is exposed to the organism, thereby customizing the catheter to the structural size of the selected site within the body.

1 Claim, 3 Drawing Sheets

U.S. PATENT DOCUMENTS

| | | | |
|---|---|---|---|
| 3,640,269 A | 2/1972 | Delgado | 128/2 R |
| 4,186,745 A | 2/1980 | Lewis et al. | 128/349 R |
| 4,300,244 A | 11/1981 | Bokros | 3/1.4 |
| 4,717,387 A | 1/1988 | Inoue et al. | 604/264 |
| 4,767,400 A | 8/1988 | Miller et al. | 604/8 |
| 4,806,182 A | 2/1989 | Rydell et al. | 156/211 |
| 4,875,468 A | 10/1989 | Krauter et al. | 128/3 |
| 4,892,538 A | 1/1990 | Aebischer et al. | 604/891.1 |
| 4,943,560 A | 7/1990 | Wigness et al. | 514/11 |
| 4,968,306 A | 11/1990 | Huss et al. | 604/264 |
| 4,976,703 A | 12/1990 | Franetzki et al. | 604/247 |
| 4,983,169 A | 1/1991 | Furukawa | 604/164 |
| 4,990,155 A | 2/1991 | Wilkoff | 606/191 |
| 4,994,047 A | 2/1991 | Walker et al. | 604/264 |
| 5,011,472 A | 4/1991 | Aebischer et al. | 604/50 |
| 5,106,627 A | 4/1992 | Aebischet et al. | 424/424 |
| 5,171,305 A | 12/1992 | Schickling et al. | 604/271 |
| 5,199,427 A | 4/1993 | Strickland | 128/207.14 |
| 5,203,776 A | 4/1993 | Durfee | 604/264 |
| 5,218,957 A | 6/1993 | Strickland | 128/200.26 |
| 5,244,619 A | 9/1993 | Burnham | 264/173 |
| 5,255,675 A | 10/1993 | Kolobow | 128/204.18 |
| 5,282,785 A | 2/1994 | Shapland et al. | 604/21 |
| 5,460,618 A | 10/1995 | Harreld | 604/264 |

* cited by examiner

METHOD FOR MANUFACTURING A CATHETER

This application is a Divisional of application Ser. No. 08/912,379 filed Aug. 18, 1997 now U.S. Pat. No. 6,093,180, which was a divisional of application Ser. No. 08/782,551 filed Jan. 10, 1997, now abandoned, which was a divisional of application Ser. No. 08/430,960 filed Apr. 28, 1995, now abandoned.

BACKGROUND OF THE INVENTION

1. Field of the Invention

In general, this invention relates to infusion catheters. More specifically, this invention relates to an intraparenchymal infusion catheter system for delivering a therapeutic agent into an organism where the catheter has a porous tip which has a perfusion surface area that may be matched to the target volume.

2. Description of the Related Art

When chronic administration of a pharmaceutically active agent is required, internal delivery by an external infusion pump or an implantable infusion pump ("IIP"), in combination with a catheter, may be the desired delivery means. For example, IIP-catheter delivery may be preferred when, for example, the site specific delivery of the drug is critical, or the drug must be administered in tightly controlled, yet minute dosages.

In current catheter designs, the delivered agent ordinarily flows out of the catheter via a fixed number of elution holes. Most catheter designs utilize either a single elution hole or a few elution holes. The current designs suffer from at least two notable disadvantages. To begin with, the fixed number of elution holes may make it difficult to tailor the catheter to the drug flow rates dictated for a particular drug and a particular parenchymal target. In many neurological applications, the quantity of delivered drug is relatively minute and must be carefully tailored. Some flexibility in flow rate is achieved by calibrating the IIP, although it is still desirable to be able to more carefully tailor the number of elution holes to the desired flow rate. In addition, current catheter designs present a fixed external perfusion surface area to a selected parenchymal target volume. Since the perfusion area is fixed, it may be difficult to match the perfusion area to the parenchymal target volume. For example, if the parenchymal target volume consists of a five centimeter long malignant mass, and the perfusion area of the catheter is only three centimeters in length, it may be very difficult to achieve infusion of a cytostatic agent through the entire length of the mass. Furthermore, there may be applications where it is desirable to minimize the volume displacement of the catheter tip into the selected parenchymal target in order to minimize tissue trauma. If the perfusion area of the catheter tip is fixed, no such tailoring is possible.

The present invention is directed at solving one or more of the above-noted problems.

SUMMARY OF THE INVENTION

A catheter system for delivering fluid to a selected site within an organism comprises a pump for delivering the fluid and a catheter coupled to the pump. The catheter comprises a first tubular portion that has a generally cylindrical lumen of a first internal diameter and is composed of a relatively impermeable material. A second tubular portion that has an open end is disposed within the lumen and a closed distal end is disposed without the lumen. The second tubular portion is composed of a flexible, porous material having a preselected microporosity that is operable to permit fluid to flow from the catheter into the organism. The second tubular portion is selectively moveable with respect to the first tubular portion.

Alternatively, a catheter for delivering fluid to a selected site within an organism comprises a first tubular portion that has a generally cylindrical lumen of a first internal diameter and is composed of a relatively impermeable material. A second tubular portion that has an open end is disposed within the lumen and a closed distal end is disposed without the lumen. The second tubular portion is composed of a flexible, porous material that has a preselected microporosity that is operable to permit fluid to flow from the catheter into the organism. The second tubular portion is selectively moveable with respect to the first tubular portion.

BRIEF DESCRIPTION OF THE DRAWINGS

Advantages of the invention will become apparent upon reading the following detailed description and references to the drawings in which.

DESCRIPTION OF THE PREFERRED EMBODIMENTS

Figure 1:
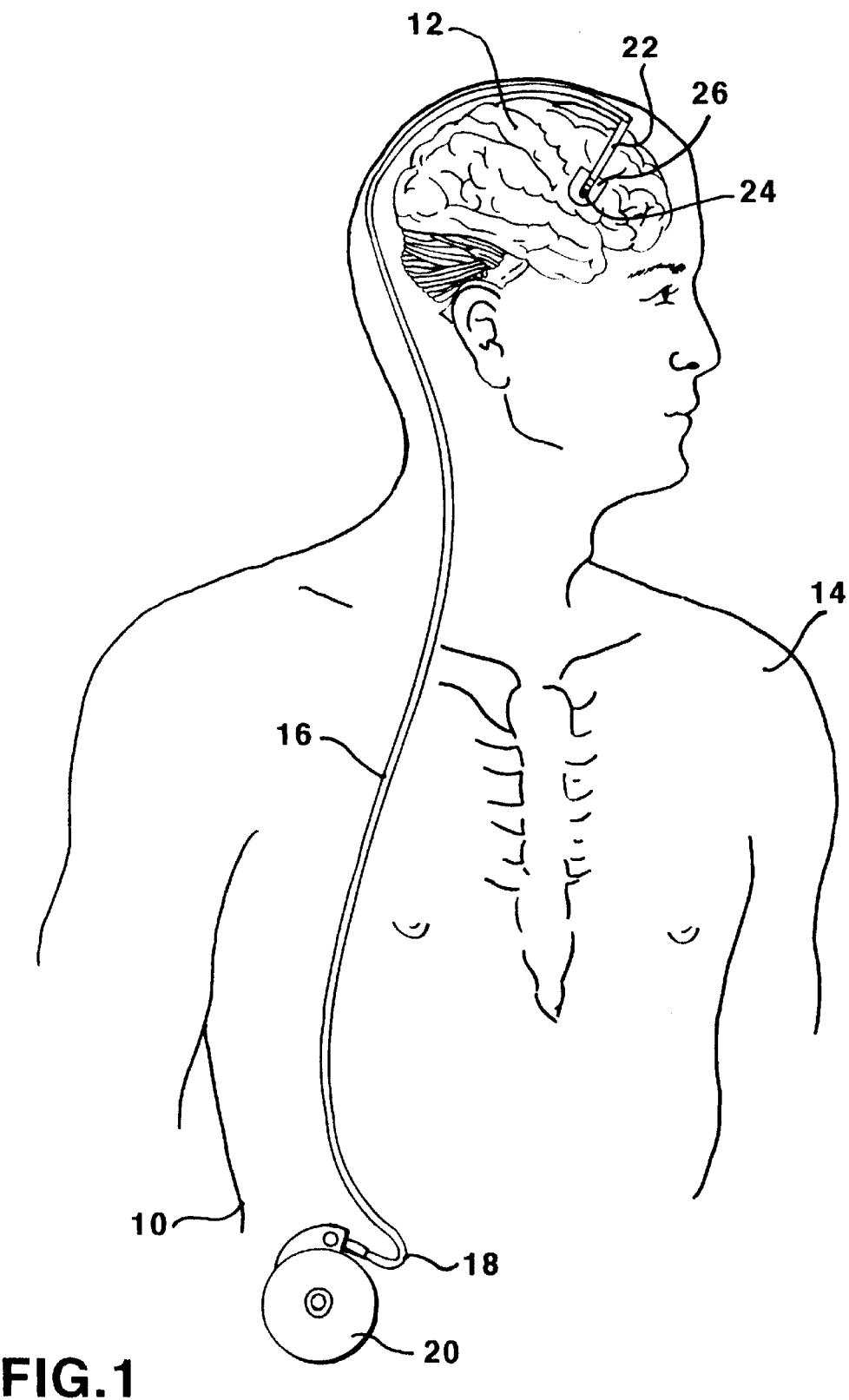
FIG. 1 depicts a preferred embodiment of the catheter system showing one possible implantation in a human body.

FIG. 1 depicts a preferred embodiment of the catheter system 10 in one possible medical application, an intracerebral placement, wherein the system 10 provides infusion of a neurological agent directly into the brain 12 in a human body 14. The catheter system 10 comprises a catheter 16 which has one end 18 coupled to an implanted infusion pump (IIP) 20 and a free distal end 22 for insertion into an organism, in this case, a human body 14. It should be understood that the system 10 could also be used on non-human animals. A catheter tip 24 is disposed at the extreme end of the distal end 22. The tip 24 has a rounded leading exterior surface to minimize tissue disruption during insertion.

Figure 1A:
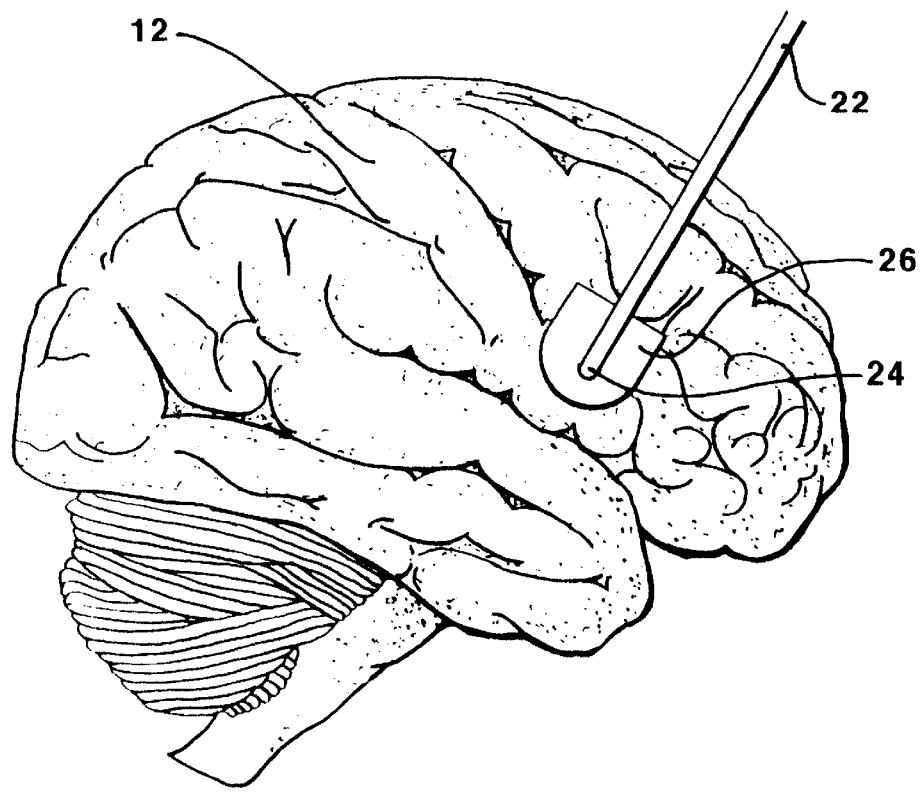
FIG. 1A depicts a schematic representation of a human brain showing placement of the tip of the catheter of the catheter system in the putamen.
Figure 2:
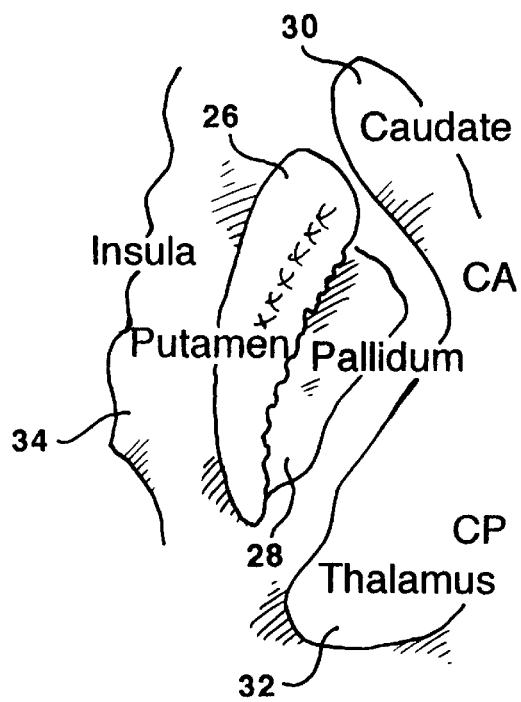
FIG. 2 is a schematic depiction of the putamen region of the human brain.

In the medical application portrayed in FIGS. 1 and 1A, the distal end 22 is intracerebrally disposed so that the tip 24 projects into the putamen 26 of the brain 12. FIG. 2 is an enlarged schematic view of a portion of the interior of the brain 12, showing the putamen 26 in relation to the pallidum 28 the caudate 30 the thalamus 32, and the insula 34, and showing schematically the placement of the tip 24. In the medical application depicted in FIGS. 1 and 2, the catheter tip 24 is positioned into the putamen 26 for retrograde access to the dopaminergic neurons contained within the retrorubral nucleus, substantia nigra, and ventral tegmentum.

The distal end 22 is surgically implanted in the brain 12 using well known stereotactic placement techniques and the catheter 16 is subsequently tunneled subcutaneously through the body 14 to the location in the body 14 where the IIP 20 will be implanted. The IIP 20 is ordinarily surgically implanted subcutaneously in the pectoral or abdominal region of the body 14. The IIP 20 may be any of a number of commercially available implantable infusion pumps such as, for example, the Syncromed pump, model 8611H, manufactured by Medtronic, Inc., Minneapolis, Minn. While an implantable IIP 20 is depicted, it should be understood to those skilled in the art that the device used to deliver agent to the catheter 16 may be either implanted or extracorporeal.

Figure 3:
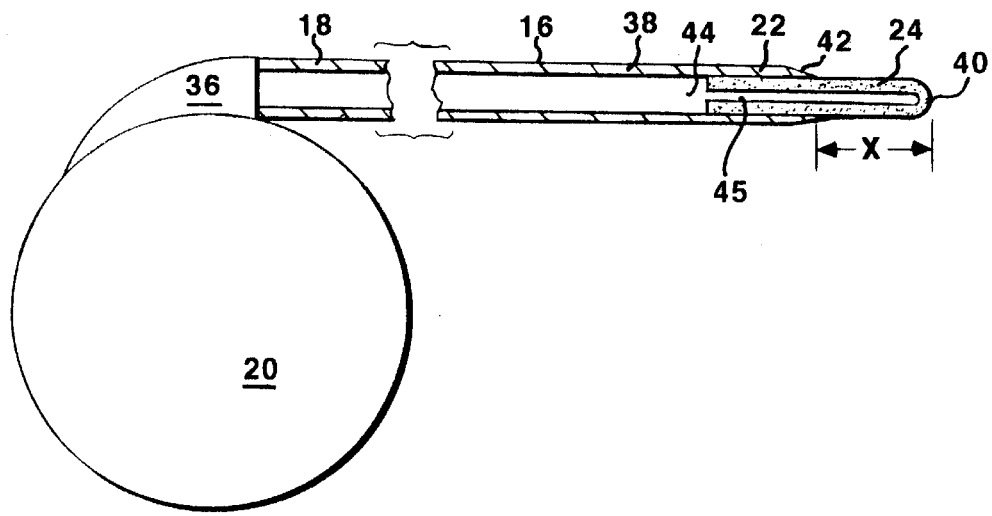
FIG. 3 depicts a preferred embodiment of the catheter system with the catheter and catheter tip illustrated in a sectional view.

The detailed structure of the catheter system 10 may be understood by reference to FIG. 3, which depicts a preferred embodiment of the catheter system 10 with the catheter 16 and the distal end 22 shown in an enlarged half section. The size of the catheter 16 and the distal end 22 are highly exaggerated for ease of illustration of the structure thereof and the full length of the catheter 16 is not shown for simplicity of illustration. The end 18 of the catheter 16 is coupled to the pump connector 36. The connection between the catheter 16 and the pump connector 36 is shown schematically in FIG. 3. It should be understood that the actual type of connection between the pump connector 36 and the catheter 16 will vary depending upon the particular type of IIP 20 utilized.

The catheter 16 comprises an elongated tubular portion 38 that extends from the pump coupling 36 and terminates in the distal end 22 and the tip 24. As noted above, the catheter tip 24 has a generally rounded leading exterior surface 40 to minimize tissue disruption during insertion. The tubular portion 38 has an externally tapered end surface 42 to again minimize tissue disruption during insertion.

The catheter tip 24 has a generally tubular shape and is designed to fit snugly within the lumen 44 of the tubular portion 30. The catheter tip 24 has a lumen 45 to receive agent from the catheter lumen 44. The catheter lumen 44 and the external diameter of the catheter tip 24 should be sized so that there is a zero tolerance therebetween. A snug fit is desirable to both maintain the position of the catheter tip 24 in relation to the tubular portion 38 and to discourage seepage of agent between the interface of the exterior of the catheter tip 24 and the interior surface of the tubular portion 38. However, as discussed more fully below, under certain conditions, the catheter 16 may be customized by moving the catheter tip 24 in relation to the tubular portion 38.

The catheter tip 24 is preferably composed of a porous material such as polysulfone hollow fiber, manufactured by Amicon, although polyethylene, polyamides, polypropylene and expanded polytetrafluorethylene (ePTFE) are also suitable. The catheter tip 24 is preferably porous along its entire length to enable agent to flow into the body 14. The preferred pore size is approximately less than or equal to 0.22 microns. It is preferred that the maximum pore size be less than or equal to approximately 0.22 microns to prevent any derelict bacterial agents that may be present inside the catheter 16 from entering into the body 14. Furthermore, at larger pore sizes, there is the potential for tissue in-growth that may restrict the flow of agents out of the catheter tip 24. By making the entire length of the catheter tip 24 porous, a more uniform volume distribution of agent is provided. Unlike an existing catheter tip that has a single elution hole or a few elution holes, the catheter tip 24 dispenses agent in a nearly 360 degree pattern along the entire length of the catheter tip 24 that is exposed to the parenchymal target, represented in FIG. 3 by the length X. Throughout this disclosure, the length of the portion of catheter tip 24 that is exposed to the parenchymal target is represented by X.

Length X may be custom selected by the physician at the time of insertion. To enable the physician to customize length X, the tubular portion 38 is composed of a material that will expand in response to an external stimulus such as heat or a chemical solvent. When the tubular portion 38 expands in response to the external stimulus, the snug fit between the catheter tip 24 and the tubular portion 38 is relieved, and the physician may slide the catheter tip 24 with respect to the tubular portion 38 by hand to achieve the desired length X. The material from which the tubular portion 38 is composed, is selected so that when the external stimulus is removed, the tubular portion 38 returns to its ordinary shape, thereby reestablishing the near zero tolerance fit between the tubular portion 38 and the catheter tip 24.

In one preferred embodiment, the tubular portion 38 is composed of a relatively impermeable material such as polyacrylonitrile. Polyacrylonitrile will expand in response to an external stimuli such as heat, and will return to its original shape upon cooling.

In an alternate preferred embodiment, the tubular portion 38 is composed of enhanced tear resistant silicone elastomer or polyurethane, which, when exposed to an external stimulus such as a chemical solvent like freon, will expand. When the solvent evaporates, the silicone elastomer or polyurethane will return to its original shape.

Whether a heat sensitive or solvent sensitive material is used, the tubular portion 38 should be biocompatible and sufficiently flexible to facilitate insertion. A durometer shore value of 80 is preferred.

In an alternate embodiment of the invention, length X may be set at the time of manufacture. In this embodiment, catheters 16 are manufactured having a variety of lengths X for the portion of catheter tip 24 that will be exposed to the parenchymal target. Lengths X are preselected to produce catheters 16 for predetermined applications. Once the length X has been determined for a catheter 16, the length X may be established on catheter tip 24 and catheter tip 24 may be attached to tubular portion 38 as described above.

The catheter system 10 is suitable for delivering a variety of agents such as the cytostatic drugs Methotrexate and Cytosine Arabinosibe and the antiseizure drug Felbamate, nerve growth factors such as glial derived neurotrophic factor (GDNF), neurotransmitters such as dopamine, acetylcholine, and antisense oligomcleotides. In selecting the catheter system 10 for use with a particular drug or agent, care should be taken to ensure that the particular agent will be compatible with the material from which the tubular portion 38 is composed.

Figure 4:
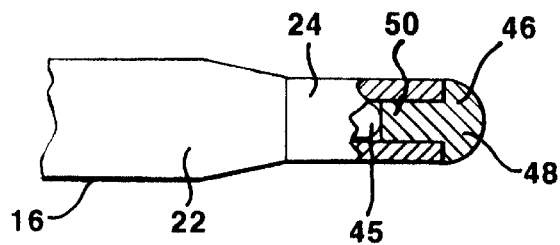
FIG. 4 depicts an alternate embodiment of the catheter system wherein the distal end of the catheter contains a radiographic marker, illustrated in partial sectional view.

FIG. 4 depicts an alternate preferred embodiment of the distal end 22 of the catheter 16, wherein a radiographic marker 46 is coupled to the tip 24. The radiographic marker 46 renders at least a portion of the tip 24 opaque to x-rays, enabling the tip 24 to be observed during fluoroscopy or via x-ray to facilitate placement of the distal end 22 and the tip 24. In a preferred embodiment, the radiographic marker 46 comprises a semispherical portion 48 that has a cylindrical nipple 50 emanating away therefrom. The semispherical portion 48 provides a rounded profile for minimizing tissue disruption during insertion. The cylindrical nipple 50 is sized to fit snugly within the lumen 45 and be held in place via a suitable biocompatible adhesive, such as a biocompatible medical silicone adhesive or a medical urethane adhesive. In a preferred embodiment, the radiographic marker 46 comprises tantalum powder dispersed in a matrix composed of a biocompatible adhesive, such as the ones discussed above. The preferred ratio of tantalum to adhesive is 3 to 2. Ordinarily, the radiographic marker 46 will be premolded prior to insertion into the lumen 45. After the radiographic marker 46 has been inserted into the lumen 45, a thin coating of the same biocompatible adhesive is preferably applied to the exterior of the semispherical portion 48. Other materials may also be suitable for the radiographic marker 46, such as barium or platinum materials.

Alternatively, the radiographic marker 46 may be composed of a material that is compatible to nuclear magnetic resonance imaging (MRI) to enable the tip 24 to be detected during an MRI scan. A preferred material for the radiographic marker 46 in an MRI context is platinum, though barium, tantalum, and similar materials are also suitable. Regardless of whether radiography or MRI is being utilized, the goal of providing a radiographic marker 46 is to enable the operator to accurately detect the precise location of the tip 24 to facilitate placement and later verification of the integrity and position of the catheter system 10.

Alternatively, the radiographic marker 46 may be composed of a material that has sufficient radio density for visualization during radiologic procedures, but in powdered form that is dispersed in the catheter tip 24 at the time the catheter tip 24 is molded.

The following example illustrates the customization feature of the catheter system 10. Assume, for the purposes of this illustration, that in the medical application depicted in FIGS. 1 and 2, the patient is suffering from Parkinson's disease and it is desired to place the catheter tip 24 in the putamen 26 of the brain 12 to deliver GDNF in a dosage of approximately 1.0 µl/h. As an initial step, the structural size of the putamen 26 can be determined by MRI. Once the structural size of the putamen 26 is determined, the physician can stimulate the tubular portion 38 to expand using the techniques discussed above and, by hand, slide the catheter tip 24 relative to the tubular portion 38 to achieve a length X that will provide maximal diffusion of the agent throughout the putamen 26 for accessing the different dopaminergic pathways. The distal end 22 and the catheter tip 24 are then positioned using known stereotactic techniques and the remainder of the catheter system 10 is placed as discussed above.

Figure 5:
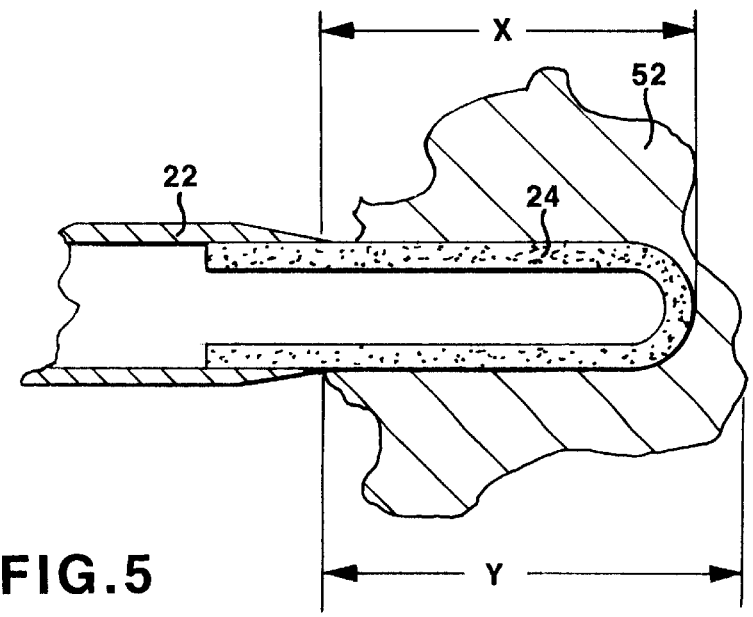
FIG. 5 depicts a portion of a preferred embodiment of the catheter system showing an alternate implantation in a human body, illustrated in a partial sectional view.

An alternate medical application is depicted in FIG. 5. FIG. 5 shows the catheter tip 24 inserted into a malignant mass 52. Assume for the purposes of this illustration that the length of the mass 52, represented by Y, is determined via a preoperative MRI. To increase the chances that a cytostatic drug such as Methotrexate will successfully destroy the malignant mass 52, it is desirable that the cytostatic agent be diffused to as much of the structure of the malignant mass 52 as possible. Therefore, it is desirable for the physician to be able to select the length of the catheter tip 24, represented by the length X, to approximate the length Y as closely as possible. As noted above, the structural size of the malignant mass 52 may be determined by a preoperative MRI. Once the structural size of the mass 52 is known, the physician can then adjust the length X using the above discussed techniques to match the length X to the length Y as closely as possible, thereby maximizing the area of the mass 52 exposed to the cytostatic agent.

Many modifications and variations may be made in the techniques and structures described and illustrated herein without departing from the spirit and scope of the present invention. For example, the system could be used to infuse a cytostatic agent into a malignant mass located in a variety of places in the body or infuse into a nerve growth factor into the intrathecal space of the spinal column. Accordingly, the techniques and structures described and illustrated herein should be understood to be illustrative only and not limiting upon the scope of the present invention.

What is claimed is:

1. A method of manufacturing a catheter comprising the steps of:
   a) forming a first tubular portion of a relatively impermeable material, the first tubular portion formed having a lumen;
   b) forming a second tubular portion of a porous material;
   c) partially disposing the second tubular portion within the lumen so that a portion of the first tubular portion overlaps the second tubular portion;
   d) adjusting the length of the second tubular portion to conform to the dimensions of a selected site in an organism, comprising the steps of:
      i) heating the first tubular portion until the diameter of the lumen increases in diameter a sufficient amount to enable relative sliding movement between the first tubular portion and the second tubular portion;
      ii) sliding the second tubular portion in the lumen relative to the first tubular portion to provide a preselected length of the second tubular portion that extends distally beyond the distal end of the first tubular portion; and
      iii) cooling the first tubular portion until the first tubular portion and the second tubular portion are no longer capable of relative sliding movement; and
   e) establishing a near zero tolerance fit between the second tubular portion and the portion of the first tubular portion that overlaps the second tubular portion.

* * * * *